(12) United States Patent
Wolff et al.

(10) Patent No.: US 7,049,142 B1
(45) Date of Patent: May 23, 2006

(54) GENE EXPRESSION WITH COVALENTLY MODIFIED POLYNUCLEOTIDES

(75) Inventors: Jon A. Wolff, Madison, WI (US); Paul M. Slattum, Madison, WI (US); James E. Hagstrom, Middleton, WI (US); Vladimir G. Budker, Middleton, WI (US)

(73) Assignee: Mirus Corporation, Madison, WI (US)

( * ) Notice: Subject to any disclaimer, the term of this patent is extended or adjusted under 35 U.S.C. 154(b) by 294 days.

(21) Appl. No.: 09/631,152

(22) Filed: Aug. 2, 2000

Related U.S. Application Data

(60) Provisional application No. 60/146,824, filed on Aug. 2, 1999.

(51) Int. Cl.
C12N 15/00 (2006.01)
C12N 15/63 (2006.01)
C12N 15/82 (2006.01)
A61K 48/00 (2006.01)

(52) U.S. Cl. ............... 435/440; 435/455; 435/468; 514/44

(58) Field of Classification Search ......... 435/440, 435/455, 468; 514/44
See application file for complete search history.

(56) References Cited

U.S. PATENT DOCUMENTS 4,950,744 A   8/1990   Dattagupta ............ 536/27

FOREIGN PATENT DOCUMENTS

WO    WO 99/13719    * 3/1999

OTHER PUBLICATIONS

Ireland et al. DNA-mediated gene transfer as an indicator of DNA damage and its repair by recipient cells. FEBS Lett. Feb. 9, 1987;212(1):173-6.*
Neves et al. Novel method for covalent fluorescent labeling of plasmid DNA that maintains structural integrity of the plasmid. Bioconjug Chem. Jan.-Feb. 2000;11(1):51-5.*
Zelphati et al. Gene chemistry: functionally and conformationally intact fluorescent plasmid DNA. Hum Gene Ther. Jan. 1, 1999;10(1):15-24.*
Emanueli et al. Angiogenesis gene therapy to rescue ischaemic tissues: achievements and future directions. Br J Pharmacol. Aug. 2001;133(7):951-8.*
Schwaab et al. Gene therapy of hemophilia. Semin Thromb Hemost. Aug. 2001;27(4):417-24.*
Rissanen et al. Gene therapy for therapeutic angiogenesis in critically ischaemic lower limb—on the way to the clinic. Eur J Clin Invest. Aug. 2001;31(8):651-66.*
Ross et al. Gene therapy in the United States: a five-year status report. Hum Gene Ther. Sep. 10, 1996;7(14):1781-90.*
Marshall Gene therapy's growing pains. Science. Aug. 25, 1995;269(5227):1050, 1052-5.*
Verma et al. Gene therapy—promises, problems and prospects. Nature. Sep. 18, 1997;389(6648):239-42.*
Pierce Chemical Technical Library "Other biotinylation reagents: Immonopure photoactivatable biotin" available at http://www.piercenet.com.*
Eck et al. Chapter 5: Gene-Based Therapy in "Goodman & Gilman's The Pharmaceutical Basis of Therapeutics", Ninth Edition, McGraw-Hill, New York.*
Orkin et al. Dec. 7, 1995, "Report and recommendations of the panel to assess teh NIH investment in research on gene therapy" available through the National Institutes of Health and online at http://www.nih.gov/news/panelrep/.*
Slattum et al. Efficient in vitro and in vivo expression of covalently modified plasmid DNA. Mol Ther. Aug. 2003;8(2):255-63.*
Chang, Alan G., et al., "Gene Therapy: Applications to the Treatment of Gastrointestinal and Liver Diseases." *Gastroenterology*; 1994; 106; pp. 1076-1084.

(Continued)

Primary Examiner—David Guzo
Assistant Examiner—Daniel M. Sullivan
(74) Attorney, Agent, or Firm—Mark K. Johnson; Kirk Ekena

(57) ABSTRACT

A process and compound wherein nucleic acids can be modified with a host of molecules and maintain their ability to be expressed. A modifying chemical attachment of polyions to polynucleotides can be used to facilitate the change of tertiary structure of the nucleic acid and in some cases condensation of nucleic acids into smaller, charged particles useful in delivering the nucleic acid to a cell.

14 Claims, 3 Drawing Sheets

OTHER PUBLICATIONS

Cheng, Sheue-yann, et al., "A Versatile Method for the Coupling of Protein to DNA: Synthesis of a-Macroglobulin-DNA Conjugates." *Nucleic Acids Research*; 1983; vol. 11, No. 3; pp. 659-669.

Chowdhury, Namita Roy, et al., "Fate of DNA Targeted to the Liver by Asialoglycoprotein Receptor-mediated Endocytosis *in Vivo*." *The Journal of Biological Chemistry*; May 25, 1993; vol. 236, No. 15, pp. 11265-11271.

Leahy, Patrick, et al., "Novel Biotinylated Plasmic Expression Vectors Retain Biological Function and Can Bind Streptavidin." *Bioconjugate Chem*; 1996; 7; pp. 545-551.

Perales, Jose Carlos, et al., "Gene Transfer *In Vivo*: Sustained Expression and Regulation of Genes Introduced Into the Liver by Receptor-Targeted Uptake." *Proc. Natl. Acad. Sci. USA, Medical Sciences*; Apr. 1994; vol. 91; pp. 4086-4090.

Sperling, Joseph, et al., "Photochemical Cross-Linking of Histones to DNA in Nuclosomes." *Nucleic Acids Research*; Aug. 1978; vol. 5, No. 8, pp. 2755-2773.

Vanin, E.F., et al., "Azicophenylglyoxal: A Heterobifunctional Photosensitive Reagent." *FEBS Letters*; Feb. 1981; vol. 124, No. 1; pp. 89-92.

Zhang, Guofeng, et al., "Efficient Expression of Naked DNA Intraarterially to Limb Muscles of Nonhuman Primates." *Human Gene Therapy*; Mar. 1, 2001; 12:000-000; pp. 427-438.

Arima H et al. "Enhancement of gene expression by the polyamidoamine dendrimer conjugates with $\alpha$-, $\beta$- and $\gamma$-cyclodextrins," Bioconjugate Chem; 2001 vol. 12 pp. 476-484.

Kihara F et al. "Effects of structure of polyamidoamine dendrimer on gene transfer efficiency of the dendrimer conjugate with $\alpha$-cyclodextrin," Bioconjugate Chem; 2002 vol. 13.pp. 1211-1219.

Klugherz BD et al. "Gene delivery from a DNA controlled-release stent in porcine coronary arteries," Nat Biotechnol; 2000 vol. 18 No. 11 pp. 1181-1184.

Rebuffat A et al. "Selective enhancement of gene transfer by steroid-mediated gene delivery," Nature Biotechnology; 2001 vol. 19 pp. 1155-1161.

Salman et al. "Kinetics and mechanism of DNA uptake into the cell nucleus," Proc Natl Acad Sci USA; 2001 vol. 98 No. 13 pp. 7247-7252.

* cited by examiner

SEQUENCE LISTING

```
<160> NUMBER OF SEQ ID NOS: 9

<210> SEQ ID NO 1
<211> LENGTH: 13
<212> TYPE: PRT
<213> ORGANISM: Simian virus 40

<400> SEQUENCE: 1

Cys Gly Tyr Gly Pro Lys Lys Lys Arg Lys Val Gly Gly
1               5                   10

<210> SEQ ID NO 2
<211> LENGTH: 39
<212> TYPE: PRT
<213> ORGANISM: Simian virus 40

<400> SEQUENCE: 2

Cys Lys Lys Lys Ser Ser Ser Asp Asp Glu Ala Thr Ala Asp Ser Gln
1               5                   10                  15

His Ser Thr Pro Pro Lys Lys Lys Arg Lys Val Glu Asp Pro Lys Asp
            20                  25                  30

Phe Pro Ser Glu Leu Leu Ser
        35

<210> SEQ ID NO 3
<211> LENGTH: 37
<212> TYPE: PRT
<213> ORGANISM: Simian virus 40

<400> SEQUENCE: 3

Cys Lys Lys Lys Trp Asp Asp Glu Ala Thr Ala Asp Ser Gln His Ser
1               5                   10                  15
```

```
Thr Pro Pro Lys Lys Arg Lys Val Glu Asp Pro Lys Asp Phe Pro
            20                  25                  30

Ser Glu Leu Leu Ser
        35

<210> SEQ ID NO 4
<211> LENGTH: 31
<212> TYPE: PRT
<213> ORGANISM: Homo sapiens

<400> SEQUENCE: 4

Cys Tyr Asn Asp Phe Gly Asn Tyr Asn Asn Gln Ser Ser Asn Phe Gly
1               5                   10                  15

Pro Met Lys Gln Gly Asn Phe Gly Gly Arg Ser Ser Gly Pro Tyr
            20                  25                  30

<210> SEQ ID NO 5
<211> LENGTH: 10
<212> TYPE: PRT
<213> ORGANISM: Human adenovirus type 5

<400> SEQUENCE: 5

Cys Lys Arg Gly Pro Lys Arg Pro Arg Pro
1               5                   10

<210> SEQ ID NO 6
<211> LENGTH: 22
<212> TYPE: PRT
<213> ORGANISM: Simian virus 40

<400> SEQUENCE: 6

Cys Lys Lys Ala Val Lys Arg Pro Ala Ala Thr Lys Lys Ala Gly Gln
1               5                   10                  15

Ala Lys Lys Lys Lys Leu
            20

<210> SEQ ID NO 7
<211> LENGTH: 14
<212> TYPE: PRT
<213> ORGANISM: Homo sapiens

<400> SEQUENCE: 7

Cys Lys Lys Lys Gly Pro Ala Ala Lys Arg Val Lys Leu Asp
1               5                   10

<210> SEQ ID NO 8
<211> LENGTH: 11
<212> TYPE: PRT
<213> ORGANISM: Simian virus 40

<400> SEQUENCE: 8

Cys Pro Lys Lys Lys Arg Lys Val Glu Asp Gly
1               5                   10

<210> SEQ ID NO 9
<211> LENGTH: 12
<212> TYPE: PRT
<213> ORGANISM: Random sequence

<400> SEQUENCE: 9

Ile Ala Glu Tyr Ile Pro Leu Glu Thr Asp Leu Gly
1               5                   10
```

GENE EXPRESSION WITH COVALENTLY MODIFIED POLYNUCLEOTIDES

This application is related to prior provisional application 60/146,824 filed on Aug. 2, 1999.

FIELD

This invention relates to the use of covalently modified polynucleotides for use in gene delivery and gene therapy applications. More specifically, polynucleotides can be modified, using a modifying chemical attachment bonding method of attachment, with a host of molecules and maintain their ability to be expressed. The modifying chemical attachment attachment, in some cases a covalent attachment, of polyions to polynucleotides can be used to facilitate the change of tertiary structure of the nucleic acid and in some cases condensation of nucleic acids into smaller, charged particles useful in delivery.

BACKGROUND

Nucleic Acid Modification

Polynucleotides can be covalently modified using a large number of different methodologies. Direct covalent attachment of molecules to polynucleotides can be accomplished by nitrogen mustards (alkylation), 2-acetylfluorene, 4-aminohydroxylamine, p-diazobenzoyl-biocytin, bisulfite activation, n-bromosuccinimide activation, EDC modification of 5' phosphates and with photobiotin (N-(4-azido-2-nitrophenyl)-aminopropyl-N'-(N-d-biotinyl-3-aminopropyl)-N'-methyl-1,3-propanediamine. Polynucleotides (DNA or RNA) can also by synthesized via in vitro enzymatic reactions to include covalently modified nucleotides. These modified nucleotides, which are incorporated into the growing polynucleotide chain, can be chemically coupled to a wide array of molecules. Some examples of molecules that can be covalently linked to polynucleotides directly or through enzymatic incorporation of modified nucleotides include; fluorescent molecules (fluorescein, rhodamine, Cy-2, Cy-3, Cy-5), peptides (i.e. nuclear localizing signals), proteins (enzymes, ligands, antibodies), lipids, sugars, carbohydrates, biotin, avidin, streptavidin, chemiluminescent substrates, digoxin and dinitrophenyl (DNP). Thus using any of these compounds or methods a vast array of molecules or compounds can be covalently attached to polynucleotides.

Nucleic Acid Alkylation

Nucleic acid alkylation results in the formation of a chemical bond between the alkylating compound (labeling reagent) and the polynucleic acid. In an alkylation reaction the polynucleic acid is incubated with the said compounds in aqueous or nonaqueous solutions, followed by separation of the labeled polynucleic acid from the unreacted alkylating reagent. The extent of alkylation can be controlled by regulating the relative amounts of alkylating reagent and polynucleic acid, by adjusting the length of the incubation, by controlling the temperature of the incubation, by controlling the absolute concentrations of polynucleic acid and alkylating reagent, and by controlling the composition of the aqueous or organic solution using solvent, pH, ionic strength, and buffers.

Gene Therapy

Delivery of functional polynucleotides or other genetic material for therapeutic purposes is gene therapy. Commercial uses of delivery and transfection processes include the purchase of such a process by a corporation or other institution for use in systems which incorporate a delivery process whether the use is for further preparation for future commercial sale or direct sale.

A polynucleotide can be delivered to a cell in order to produce a cellular change that is therapeutic. Polynucleotides may be coded to express a whole or partial protein, or may be anti-sense, and can be delivered either directly to the organism in situ or indirectly by transfer to a cell that is then transplanted into the organism. The protein can be missing or defective in an organism as a result of a genetic, inherited or acquired defect in its genome.

For example, a polynucleotide may be coded to express the protein dystrophin that is missing or defective in Duchenne muscular dystrophy. The coded polynucleotide is delivered to a selected group or groups of cells and incorporated into those cell's genome or remain apart from the cell's genome. Subsequently, dystrophin is produced by the formerly deficient cells. Other examples of imperfect protein production that can be treated with gene therapy include the addition of the protein clotting factors that are missing in the hemophilias and enzymes that are defective in inborn errors of metabolism such as phenylketonuria (PKU).

A delivered polynucleotide can also be therapeutic in acquired disorders such as neurodegenerative disorders, cancer, heart disease, and infections. The polynucleotide has its therapeutic effect by entering the cell. Entry into the cell is required for the polynucleotide to produce the therapeutic protein, to block the production of a protein, or to decrease the amount of a RNA. Other therapeutic genes can be erythropoietin, vascular growth factors such as fibroblast growth factor (FGF) or vascular endothelial growth factor (VEGF).

A delivered polynucleotide can also be therapeutic by stimulating or inducing a strong immune response against a desired foreign antigen. The polynucleotide has its therapeutic effect by entering the cell and being expressed into protein. This protein, upon being recognized as "foreign" by the immune system stimulates the production of both antibody and/or cell mediated protective responses against the expressed protein.

Additionally, a polynucleotide can be delivered to block gene expression. Such polynucleotides can be anti-sense by preventing translation of a messenger RNA or could block gene expression by preventing transcription of the gene. Preventing RNA translation and/or DNA transcription is considered preventing expression. Transcription can be blocked by the polynucleotide binding to the gene as a duplex or triplex. It could also block expression by binding to proteins that are involved in a particular cellular biochemical process.

Polynucleotides may be delivered that recombine with genes. The polynucleotides may be DNA, RNA, hybrids and derivatives of natural nucleotides. Recombine is the mixing of the sequence of a delivered polynucleotide and the genetic code of a gene. Recombine includes changing the sequence of a gene.

Delivery of a polynucleotide means to transfer a polynucleotide from a container outside a mammal to within the outer cell membrane of a cell in the mammal. The term transfection is used herein, in general, as a substitute for the term delivery, or, more specifically, the transfer of a polynucleotide from directly outside a cell membrane to within the cell membrane. If the polynucleotide is a messenger RNA, a ribosome translates the messenger RNA to produce a protein within the cytoplasm. If the polynucleotide is a DNA, it enters the nucleus where it is transcribed into a messenger RNA that is transported into the cytoplasm where it is translated into a protein. The polynucleotide contains sequences that are required for its transcription and translation. These include promoter and enhancer sequences that are required for initiation. DNA and thus the corresponding mRNA (transcribed from the DNA) contains introns that must be spliced, poly A addition sequences, and sequences required for the initiation and termination of its translation into protein. Therefore if a polynucleotide expresses its cognate protein, then it must have entered a cell.

A therapeutic effect of the protein in attenuating or preventing the disease state can be accomplished by the protein either staying within the cell, remaining attached to the cell in the membrane or being secreted and dissociating from the cell where it can enter the general circulation and blood. Secreted proteins that can be therapeutic include hormones, cytokines, growth factors, clotting factors, antiprotease proteins (e.g. alpha-antitrypsin) and other proteins that are present in the blood. Proteins on the membrane can have a therapeutic effect by providing a receptor for the cell to take up a protein or lipoprotein. For example, the low density lipoprotein (LDL) receptor could be expressed in hepatocytes and lower blood cholesterol levels by removing excess LDL from the blood and thereby prevent atherosclerotic lesions that can cause strokes or myocardial infarction. Therapeutic proteins that stay within the cell can be enzymes that clear a circulating toxic metabolite as in phenylketonuria. They can also cause a cancer cell to be less proliferative or cancerous (e.g. less metastatic). A protein within a cell could also interfere with the replication of a virus.

The terms "therapeutic" and "therapeutic results" are defined in this application as levels of gene products, including reporter (marker) gene products, which indicate a reasonable expectation of gene expression using similar compounds (nucleic acids), at levels considered sufficient by a person having ordinary skill in the art of gene therapy. For example: Hemophilia A and B are caused by deficiencies of the X-linked clotting factors VIII and IX, respectively. Their clinical course is greatly influenced by the percentage of normal serum levels of factor VIII or IX: <2%, severe; 2–5%, moderate; and 5–30% mild. This indicates that in severe patients only 2% of the normal level can be considered therapeutic. Levels greater than 6% prevent spontaneous bleeds but not those secondary to surgery or injury. A person having ordinary skill in the art of gene therapy would reasonably anticipate therapeutic levels of expression of a gene specific for a disease based upon sufficient levels of marker gene results. In the Hemophilia example, if marker genes were expressed to yield a protein at a level comparable in volume to 2% of the normal level of factor VIII, it can be reasonably expected that the gene coding for factor VIII would also be expressed at similar levels.

Nucleic Acids (Polynucleotides)

The term nucleic acid is a term of art that refers to a string of at least two base-sugar-phosphate combinations. (A polynucleotide is distinguished, here, from an oligonucleotide by containing more than 120 monomeric units.) The term includes deoxyribonucleic acid (DNA) and ribonucleic acid (RNA). Nucleotides are the monomeric units of nucleic acid polymers. Anti-sense is a polynucleotide that interferes with the function of DNA and/or RNA. Natural polynucleotides have a phosphate backbone, artificial polynucleotides may contain other types of backbones, but contain the same bases. RNA may be in the form of an tRNA (transfer RNA), snRNA (small nuclear RNA), rRNA (ribosomal RNA), mRNA (messenger RNA), anti-sense RNA, and ribozymes. DNA may be in form plasmid DNA, viral DNA, linear DNA, or chromosomal DNA or derivatives of these groups. In addition to these forms; DNA and RNA may be single, double, triple, or quadruple stranded. The term also includes PNAs (peptide nucleic acids), phosphorothioates, and other variants of the phosphate backbone of native nucleic acids.

A delivered DNA can stay within the cytoplasm or nucleus apart from the endogenous genetic material. Alternatively, the DNA could recombine (become a part of) the endogenous genetic material. For example, DNA can insert into chromosomal DNA by either homologous or non-homologous recombination.

Condensation of DNA

A large number of multivalent cations with widely different molecular structures have been shown to induce change in the tertiary structure of DNA including condensation.

Two approaches are currently used for compacting (condensing) DNA:

1. Multivalent cations with a charge of three or higher have been shown to condense DNA. These include spermidine, spermine, $Co(NH_3)_6^{3+}$, $Fe^{3+}$, and natural or synthetic polymers such as histone H1, protamine, polylysine, and polyethylenimine. Analysis has shown DNA condensation to be favored when 90% or more of the charges along the sugar-phosphate backbone are neutralized by the polycation.

2. Polymers (neutral or anionic) which can increase repulsion between DNA and its surroundings have been shown to compact DNA. Most significantly, spontaneous DNA self-assembly and aggregation process have been shown to result from the confinement of large amounts of DNA, due to excluded volume effect.

Depending upon the concentration of DNA, condensation leads to three main types of structures:
  1) In extremely dilute solution (about 1 ug/ml or below), long DNA molecules can undergo a monomolecular collapse and form structures described as toroids.
  2) In very dilute solution (about 10 ug/ml) microaggregates form with short or long molecules and remain in suspension. Toroids, rods and small aggregates can be seen in such solution.
  3) In dilute solution (about 1 mg/ml) large aggregates are formed that sediment readily.

Toroids have been considered an attractive form for gene delivery because they have the smallest size. While the size of DNA toroids produced within single preparations has been shown to vary considerably, toroid size is unaffected by the length of DNA being condensed. DNA molecules from 400 bp to genomic length produce toroids comparable in size. Therefore one toroid can include from one to several DNA molecules. The kinetics of DNA collapse by polycations that resulted in toroids is very slow. For example DNA condensation by $Co(NH_3)_6Cl_3$ needs 2 hours at room temperature.

The mechanism of DNA condensation is not obvious. The electrostatic force between unperturbed helices arises primarily from a counterion fluctuation mechanism requiring multivalent cations and plays a major role in DNA condensation. The hydration forces predominate over electrostatic forces when the DNA helices approach closer then a few water diameters. In the case of DNA—polymeric polycation interactions, DNA condensation is a more complicated process than the case of low molecular weight polycations. Different polycationic proteins can generate toroid and rod formation with different size DNA at a ratio of positive to negative charge of 0.4. T4 DNA complexes with polyarginine or histone can form two types of structures; an elongated structure with a long axis length of about 350 nm (like free DNA) and dense spherical particles. Both forms exist simultaneously in the same solution. The reason for the co-existence of the two forms can be explained as an uneven distribution of the polycation chains among the DNA molecules. The uneven distribution generates two thermodynamically favorable conformations. The electrophoretic mobility of DNA-polycation complexes changes from negative to positive when there is an excess of polycation. This results in DNA condensation and particle formation and the DNA-polycation complexes remain in the well during electrophoresis In the absence of an excess of a polycation or oligocation, the DNA remains unaggregated and the DNA and polycations can dissociate allowing the DNA to migrate into an agarose gel during electrophoresis. In DNA/polycation complexes (not covalently or chemically attached) it is likely that the large polycations don't completely align along DNA but form polymer loops that interact with other DNA molecules. The rapid aggregation and strong intermolecular forces between different DNA molecules may prevent the slow adjustment between helices needed to form tightly packed orderly particles.

Transfection Reagents

A transfection reagent is a compound or compounds used in the prior art that bind(s) to or complex(es) with polynucleotides and mediates their entry into cells. The transfection reagent also mediates the binding and internalization of polynucleotides into cells. Examples of transfection reagents include cationic liposomes and lipids, amphipathic polyamines, polyethylenimine, calcium phosphate precipitates, and polylysine complexes. Typically, the transfection reagent has a net positive charge that binds to the polynucleotide's negative charge. The transfection reagent mediates binding of polynucleotides to cells via its positive charge (that binds to the cell membrane's negative charge) or via ligands that bind to receptors in the cell. For example, cationic liposomes or polylysine or polyethylenimine (PEI) complexes have net positive charges that enable them to bind to DNA. Other vehicles are also used, in the prior art, to transfer genes into cells. These include complexing the polynucleotides on particles that are then accelerated into the cell. This is termed biolistic or gun techniques. Other methods include electroporation in which a device is used to provide a electric current or charge to cells.

Naked DNA

Naked DNA can also be used for gene therapy. The term, naked DNA or polynucleotides, indicates that the polynucleotides are not associated with a transfection reagent or other delivery vehicle that is required for the polynucleotide to be delivered to the parenchymal cell. The naked DNA can be delivered by direct intraparenchymal injection into the tissue or can be delivered by an intravascular route. These tissues can include striated muscle (e.g. heart and skeletal muscle), liver, lung, intestines, brain, adrenal glands, thymus, kidneys, brain, spinal cord, peripheral nerves, endothelial cells, blood vessels, spleen, gonads, thyroid, skin, pancreas, salivary glands, eyes, mucosal membranes, vagina, bladder, prostate, cancer cells, tumors, neoplastic tissue, and blood cells (e.g. leukocytes, platelets, red blood cells).

Vectors

Vectors are polynucleic acid molecules originating from a virus, a plasmid, or the cell of a higher organism into which another nucleic fragment of appropriate size can be integrated; vectors introduce foreign DNA into host cells, where it can be reproduced. Examples are plasmids, cosmids, and yeast artificial chromosomes; vectors are often recombinant molecules containing DNA sequences from several sources. A vector includes a viral vector: for example, adenovirus (icosahedral (20-sided) virus that contains dsDNA; there are over 40 different adenovirus varieties, some of which cause the common cold); adenoassociated viral vectors (AAV) which are derived from adenoassociated viruses and are smaller than adenoviruses; and retrovirus (any virus in the family Retroviridae that has RNA as its nucleic acid and uses the enzyme reverse transcriptase to copy its genome into the DNA of the host cell's chromosome; examples include VSV G and retroviruses that contain components of lentivirus including HIV type viruses).

Polymers

Polymers are used for drug delivery for a variety of therapeutic purposes. Polymers have also been used in research for the delivery of nucleic acids (polynucleotides and oligonucleotides) to cells with an eventual goal of providing therapeutic processes. Such processes have been termed gene therapy or anti-sense therapy. One of the several methods of nucleic acid delivery to the cells is the use of DNA-polycations complexes. It has been shown that cationic proteins like histones and protamines or synthetic polymers like polylysine, polyarginine, polyornithine, DEAE dextran, polybrene, and polyethylenimine may be effective intracellular delivery agents while small polycations like spermine are ineffective. The following are some important principles involving the mechanism by which polycations facilitate uptake of DNA. Protein refers to a linear series of greater than 50 amino acid residues connected one to another as in a polypeptide.

Polycations provide attachment of DNA to the target cell surface. The polymer forms a cross-bridge between the polyanionic nucleic acids and the polyanionic surfaces of the cells. As a result the main mechanism of DNA translocation to the intracellular space might be non-specific adsorptive endocytosis which may be more effective then liquid endocytosis or receptor-mediated endocytosis. Furthermore, polycations are a convenient linker for attaching specific receptors to DNA and as result, DNA-polycation complexes can be targeted to specific cell types.

Polycations protect DNA in complexes against nuclease degradation. This is important for both extra- and intracellular preservation of DNA. The endocytic step in the intracellular uptake of DNA-polycation complexes is suggested by results in which DNA expression is only obtained by incorporating a mild hypertonic lysis step (either glycerol or DMSO). Gene expression is also enabled or increased by preventing endosome acidification with $NH_4Cl$ or chloroquine. Polyethylenimine, which facilitates gene expression without additional treatments, probably disrupts endosomal function itself. Disruption of endosomal function has also been accomplished by linking to the polycation endosomal-disruptive agents such as fusion peptides or adenoviruses.

Polycations facilitate DNA condensation. The volume which one DNA molecule occupies in complex with polycations is drastically lower than the volume of a free DNA molecule.

A Lewis acid:Lewis base complex is an electron pair acceptor:electron pair donor.

A transition metal is a group of metallic elements in which the members have the filling of the outermost shell to eight electrons interrupted to bring the penultimate shell from 8 to 18 or 32 electrons and this includes elements 21–29 and 29–47 and 57–79 and all known elements from 89 on.

A chemical attachment is defined in this specification as a covalent, noncovalent bond or pi stacking between two atoms.

In this specification, a modifying chemical attachment is a chemical attachment, including a Lewis acid:Lewis base attachment but does not include electrostatic binding, hydrogen bonding, pi stacking, minor groove binding or intercalation.

Routes of Administration

An intravascular route of administration enables a polymer or polynucleotide to be delivered to cells more evenly distributed and more efficiently expressed than direct injections. Intravascular herein means within a tubular structure called a vessel that is connected to a tissue or organ within the body. Within the cavity of the tubular structure, a bodily fluid flows to or from the body part. Examples of bodily fluid include blood, lymphatic fluid, or bile. Examples of vessels include arteries, arterioles, capillaries, venules, sinusoids, veins, lymphatics, and bile ducts. The intravascular route includes delivery through the blood vessels such as an artery or a vein (U.S. patent application Ser. No. 08/975,573 is incorporated herein by reference).

An administration route involving the mucosal membranes is meant to include nasal, bronchial, inhalation into the lungs, or via the eyes.

SUMMARY

The Use of Chemically? Modified DNA for Nucleic Acid Delivery, Integration, and Gene Expression Utilizing Modifying chemical attachment Bonding Chemistry Efficient transport of polynucleotides into cells is vital for effective gene therapy. Since covalently modified nucleic acids can be expressed efficiently within cells, covalent modification of polynucleotides may be used to enhance cellular gene expression. Nucleic acids can also be modified at specific locations via modifying chemical attachment non-covalent attachment chemistries like cis-platinum. By modifying polynucleotides (i.e. DNA, RNA or oligonucleotides) using modifying chemical attachment bonding chemistry, it is possible to attach a wide array of molecules (i.e. signals) that enhance uptake, expression or antisense activities of DNA, RNA or oligonucleotides in cells. Signals can be attached to polynucleotides that augment cell binding, cell internalization, endosome escape, cytoplasmic transport, nuclear localization, nuclear retention and/or gene expression (see signal section). Covalent modifications may also facilitate recombination of the delivered (modified) DNA with the endogenous unmodified DNA thus facilitating integration of the delivered DNA into the host chromosomes. Covalent attachment of polycations to nucleic acids can also be used to decrease the size of DNA-polycation complex.

In a preferred embodiment, polynucleotides (DNA or RNA or oligonucleotides) are covalently modified either within or outside of an expressible sequence to contain specific signals that enhance one or more of the following activities; cellular uptake, cytoplasmic transport, nuclear localization, gene expression, or chromosomal integration.

The Use of Modified DNA Utilizing Modifying Chemical Attachment Bonding Chemistry To Generate an Augmented Immune Response Against an Expressed Polypeptide.

Gene based vaccines are currently being extensively studied as an attractive alternative to viral or protein based vaccines. For gene based vaccines to be useful, a robust immune response against the encoded "foreign" protein must be generated by the recipient organism. It is possible that chemical modification of DNA with any of a wide range of compounds or unusual conformations such as Z-DNA may induce immune response (K. Moelling, Gene Therapy, 5:573–574, 1998). The ability to chemically modify an expressible gene sequence with any of a wide range of signals or reactive species while maintaining it's ability to be expressed into a polypeptide provides a new and powerful method for augmenting gene based immune responses.

Cellular Delivery of Modified Polynucleotides Utilizing Modifying chemical Attachment Bonding Chemistry Modified polynucleotides for use in gene therapy can be delivered to cells using the same methods used to deliver unmodified polynucleotides. These include delivery of naked polynucleotides through intravascular, intraperitoneal, intramuscular, oral, or direct intraparenchymal injections. Covalently modified polynucleotides for use in gene therapy can also be delivered to cells after complexing with cationic lipids, cationic polymers, cationic protein, transfection reagents, amphipathic polyamines, polyethylenimine and others. Covalently modified polynucleotides can also be delivered to cells after sequestration inside cationic, anionic or neutral liposomes, after inclusion within non-viral polyelectrolyte particles consisting of cationic and/or anionic polymers and/or cationic and/or polyanionic proteins. The covalently modified DNA is functional following delivery to cells in either a condensed state (see example 1) or in an uncondensed state (see examples 3 and 4).

Modified nucleic acids that retain the ability to be expressed have many uses. Modified nucleic acids can be targeted to specific cell types by attaching targeting ligands. Any ligand with specificity for a given cell or tissue type would be applicable. Some examples include, ligands targeting the asialoglycoprotein receptor of liver cells, cell type specific integrins on nearly any cell type, folate receptor on tumor cells, CD4 receptor on lymphoid cells, etc. The modifications can also result in increased expression by directing the nucleic acid to the nucleus where transcription takes place. This is accomplished by attaching nuclear locating peptides (NLS) to the nucleic acid. Escape of the nucleic acid from the endosome may be enhanced by attaching endosomal disrupting peptides or other compounds to the nucleic acid. Delivery to cells in vivo can be enhanced by the attachment of cationic or anionic charge to the nucleic acid resulting in a change in tertiary structure of the nucleic acid. A change in tertiary structure may lead to increased resistance to DNases, and an increased rate of egress from the bloodstream as a result of reduced radius of gyration (i.e. size). Furthermore, DNA compaction can be gained by attaching reactive groups such as sulfhydryls to the nucleic acid. The sulfhydryls can then be oxidized into disulfides resulting in a crosslinked compacted nucleic acid. Upon delivery to the cell cytoplasm these disulfides would be reduced by intracellular reduction pathways (both glutathione dependent and glutathione independent pathways) thereby returning the nucleic acid to it's native conformation. Any of the signals, ligands, peptides, or molecules attached to the nucleic acid can be attached to the nucleic acid in a reversible manner. This allows removal of the attached group at a desired location, for example a pH sensitive linkage between the nucleic acid reactive group and the signal/functional group could be used to release the attached group in areas of low pH such as the interior of endosomes or near tumors. Disulfide linkages could be used to release attached groups in the cytoplasm of cells. For example a multiply charged group such as di or tri-lysine could be attached to the Label IT® molecule via a disulfide linkage. The nucleic acid would then be compacted during delivery of the nucleic acid to the cell. Once the nucleic acid escapes the endosome the disulfide linkages would be reduced, returning the nucleic acid to its native conformation.

DETAILED DESCRIPTION

Figure 1:
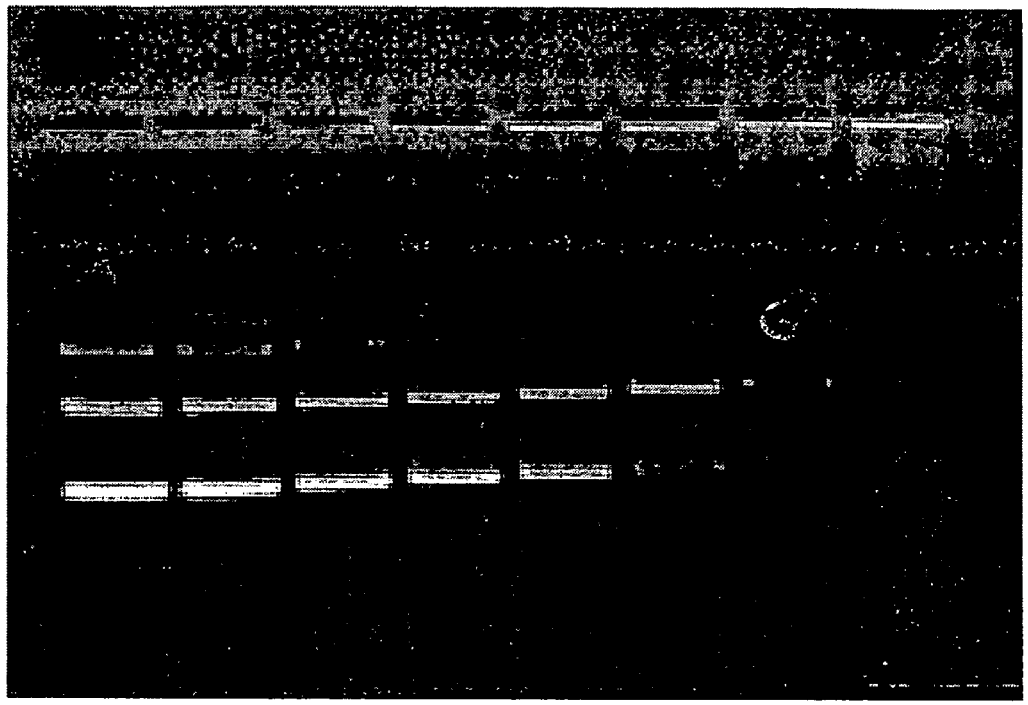
FIG. 1 is a print of an Agarose gel of DNA covalently modified with (4+) LabelIT® Monomer.

The present invention relates to a process of modifying a gene (either within or outside an expressible sequence) such that the gene can be efficiently expressed in a cell. The expressible gene sequence which is modified can be a part of circular piece of DNA such as a plasmid, or a linear piece of DNA. The expressible sequence can be modified with any of a wide range of compounds. Compounds can be attached to nucleic acids for a number of different reasons including: marking of the gene sequence for identification within cells, to augment it's delivery into the cell over that of unmodified sequences, or to facilitate increased expression of the gene product. A compound can also be attached that would increase the frequency of stable integration of the modified DNA into the genomic DNA of an organism over that which is obtained with unmodified DNA. Efficient stable integration of labeled DNA is highly desirable for creating stable cell transfectants in vitro, transgenic animals, transgenic plants or for gene therapy purposes. DNA can be efficiently modified covalently on the N7 position of guanine using alkylating agents such as nitrogen mustards, sulfur mustards, epoxides, aziridines, episulfides, dimethylsulfate, molecules containing activated cyclopropyl groups such as the CPI family of molecules, bromoacetamides, or non-covalently using cis-platinum based reagents. Expressible gene sequences modified on the N7 position of guanine can be efficiently expressed following introduction into cells.

In one preferred embodiment, compounds are attached to DNA at the N7 position and the expressible sequence remains functional upon introduction into a cell.

The present invention also relates to a process of delivering the modified gene to a cell. Delivering a gene means that the gene is placed in a position to become associated with the cell. The gene can be on the membrane of the cell or inside the cytoplasm, nucleus, or other organelle of the cell. The process of delivering a gene to a cell has also been commonly termed "transfection" or the process of "transfecting" and also it has been termed "transformation." The cell can be a mammalian cell that is within the tissue in situ. The cell can also have been removed and maintained in tissue culture in a primary, secondary, immortalized or transformed state.

The gene, as used in this specification, is a unit of coded information usually used to make a functional product. It is a polynucleotide and can be double-stranded DNA, single-stranded DNA, or a messenger RNA. The double-stranded DNA is typically derived from either plasmid DNA in bacteria or from polymerase chain reaction amplification (PCR). These polynucleotides contain a coding sequence for a polypeptide or protein and the associated sequences required for expression. For the DNA this includes a promoter, enhancer, 5' untranslated regions, 3' untranslated regions, introns, poly A addition site and transcription terminators. For RNA, a promoter, enhancer, poly A addition site, or transcription terminator would not be necessary. An oligonucleotide such as an antisense molecule that doesn't express a protein is excluded from this definition of a gene.

Attachment of a Signal Molecule to a Gene without Preventing its Expression

The gene transfer enhancing signal is attached utilizing modifying chemical attachment bonding chemistry such as a covalent bond to the gene using a variety of methods. They can be alkylating reagents or photoactivatable compounds. Examples of alkylating reagents include the use of mustards and the use of compounds containing the CPI DNA alkylating moiety (cyclopropa-pyrrolo-indol) and its derivatives. All compounds in the CPI family include the functionality: 1,2,8,8a-tetrahydro-7-methylcyclopropa-[c]pyrrolo-[3,2-e] indol-4(5H)-one.

Mustards are molecules consisting of a nucleophile and a leaving group separated by an ethylene bridge. After internal attack of the nucleophile on the carbon bearing the leaving group a strained three membered group is formed. This strained ring (in the case of nitrogen mustards an aziridine ring is formed) is very susceptible to nucleophilic attack. Thus allowing mustards to alkylate weak nucleophiles such as polynucleic acids. Mustards can have one of the ethylene bridged leaving groups attached to the nucleophile, these molecules are sometimes referred to as half-mustards; or they can have two of the ethylene bridged leaving groups attached to the nucleophile, these molecules can be referred to as bis-mustards. One class of mustards are R-chloride derivatives that contain the aromatic nitrogen mustard 4-[(2-chloroethyl)-methylamino]-benzylamine. We incorporate herein by reference a patent application entitled: A Method for Single-Step Attachment of a

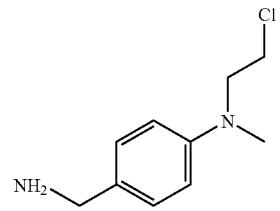

Label to Target Molecules, Ser. No. 09/982,485.

R-chloride

A gene can be modified within the sequences required for expression. Expression as used in this specification means the transcription of the gene into RNA or the translation of RNA into protein. DNA sequences necessary for expression or transcription include sequences such as promoters, enhancers, 5' untranslated regions, 3' untranslated regions, introns, poly A addition site and transcription terminators. Modification within the expression cassette does not prevent expression of the gene. In one preferred embodiment, this can be accomplished by first chemically modifying a piece of DNA which contains an expressible sequence such as an entire plasmid. Thus the attachment can be to sequences either within or outside the sequences required for expression.

Gene Transfer Enhancing Signals

In a preferred embodiment, a chemical reaction can be used to attach a gene transfer enhancing signal to a nucleic acid The gene transfer enhancing signal (or abbreviated as the Signal) is defined in this specification as a molecule that modifies the nucleic acid complex for more efficient delivery to a location (such as tissue) or location in a cell (such as the nucleus) either in culture or in a whole organism. By modifying the cellular or tissue location of the foreign gene, the expression of the foreign gene can be enhanced.

The gene transfer enhancing signal can be a protein, peptide, lipid, steroid, sugar, carbohydrate, (non-expresssing) polynucleic acid or synthetic compound. The gene transfer enhancing signals enhance cellular binding to receptors, cytoplasmic transport to the nucleus and nuclear entry or release from endosomes or other intracellular vesicles.

Nuclear localizing signals enhance the targeting of the gene into proximity of the nucleus and/or its entry into the nucleus. Such nuclear transport signals can be a protein or a peptide such as the SV40 large T antigen NLS or the nucleoplasmin NLS. These nuclear localizing signals interact with a variety of nuclear transport factors such as the NLS receptor (karyopherin alpha) which then interacts with karyopherin beta. The nuclear transport proteins themselves could also function as NLS's since they are targeted to the nuclear pore and nucleus. For example, karyopherin beta itself could target the DNA to the nuclear pore complex. Several peptides have been derived from the SV40 T antigen. These include a short NLS SEQ ID NO:1 (H-CGYG-PKKKRKVGG-OH) or long NLS's SEQ ID NO:2 (H-CK-KKSSSDDEATADSQHSTPPKKKRKVEDPKDFPSELLS-OH and SEQ ID NO: 3H-CKKKWDDEATADSQHSTPP-KKKRKVEDPKDFPSELLS-OH). Other NLS peptides have been derived from M9 protein SEQ ID NO: 4 (CYN-DFGNYNNQSSNFGPMKQGNFGGRSSGPY), E1A SEQ ID NO: 5 (H-CKRGPKRPRP-OH), nucleoplasmin SEQ ID NO: 6 (H-CKKAVKRPAATKKAGQAKKKKL-OH), and c-myc SEQ ID NO: 7 (H-CKKKGPAAKRVKLD-OH).

Signals that enhance release from intracellular compartments (releasing signals) can cause DNA release from intracellular compartments such as endosomes (early and late), lysosomes, phagosomes, vesicle, endoplasmic reticulum, golgi apparatus, trans golgi network (TGN), and sarcoplasmic reticulum. Release includes movement out of an intracellular compartment into cytoplasm or into an organelle such as the nucleus. Releasing signals include chemicals such as chloroquine, bafilomycin or Brefeldin A1 and the ER-retaining signal (KDEL sequence), viral components such as influenza virus hemagglutinin subunit HA-2 peptides and other types of amphipathic peptides.

Cellular receptor signals are any signal that enhances the association of the gene with a cell. This can be accomplished by either increasing the binding of the gene to the cell surface and/or its association with an intracellular compartment, for example: ligands that enhance endocytosis by enhancing binding the cell surface. This includes agents that target to the asialoglycoprotein receptor by using asiolyglycoproteins or galactose residues. Other proteins such as insulin, EGF, or transferrin can be used for targeting. Peptides that include the RGD sequence can be used to target many cells. Chemical groups that react with sulfhydryl or disulfide groups on cells can also be used to target many types of cells. Folate and other vitamins can also be used for targeting. Other targeting groups include molecules that interact with membranes such as lipids fatty acids, cholesterol, dansyl compounds, and amphotericin derivatives. In addition viral proteins could be used to bind cells.

In a preferred embodiment, a complex is formed by using a modifying chemical attachment for attaching a plurality of compound to a nucleic acid in an amount sufficient to change the tertiary structure of the nucleic acid. The change in tertiary structure allows for more efficient delivery of the complex to a cell, in vivo, when compared to compound attachment where the attachment is less strong such as ionic bonding.

In a preferred embodiment, a process for nucleic acid delivery includes preparing a nucleic acid molecule having an expressible sequence. A compound is attached to the nucleic acid molecule within the expressible sequence which allows more than 40% expression of the expressible sequence as compared to the nucleic acid without compound attachment. The nucleic acid is delivered to a cell where the expressible sequence may be expressed.

In a preferred embodiment a signal is covalently attached to a plasmid (i.e. circular polynucleotide) randomly at a position either within or outside of the expressible sequence of the plasmid.

In another preferred embodiment the signal is attached to a polynucleotide either within or outside the expressible sequence and the signal is selected from a group of compounds that stimulate an enhanced immune reaction against the protein encoded by the expressible sequence.

In another preferred embodiment a polycation is covalently attached to a polynucleotide resulting in DNA compaction and negatively charged particles formation. The attachment of the polycation allows for the formation of DNA particles that have a different tertiary (3-dimensional) conformation than particles formed by non-covalent interactions. In one This indicates that charge neutralization is not required and particle formation is not the result of charge mediated DNA condensation.

EXAMPLE 1

DNA covalently modified (alkylated) with rhodamine is efficiently expressed in COS 7 cells following transfection.

Methods.

DNA labeling—Rhodamine molecules were covalently attached to plasmid DNA (pCILuc) encoding the reporter gene luciferase through an alkylation reaction. The plasmid, pCILuc was mixed with LabelIT® Rhodamine (Mirus Corporation, Madison Wis.) at three different ratios (1:0.2; 1:0.1; 1:0.05) (wt:wt) and incubated for 30 minutes at 37° C. Rhodamine-labeled DNA was purified and concentrated by ethanol precipitation. Rhodamine-labeling was confirmed by agarose gel electrophoresis in which a mobility shift of all rhodamine-labeled DNA was observed (data not shown).

Luciferase expression—For gene expression studies rhodamine-labeled DNA was complexed with the transfection reagent TransIT LT-1 (Mirus Corporation) at a 1:3 (wt:vol) ratio and added to COS 7 cells according to manufacturer's recommendations. Transfected cells were grown at 37° C. for 48 hours and harvested into luciferase buffer (0.1M KPO4, pH 7.8; 1 mM DTT; 0.1% Triton X-100). Cell lysates were assayed for luciferase activity on a luminometer (Lumat LB 9507, EG&G Berthold).

Results.

LabelIT® rhodamine facilitates the attachment of rhodamines primarily at guanine nucleotides so labeling occurs throughout the plasmid. The different levels of labeling that was used results in the covalent attachment of about 1 rhodamine per 30—120 base pairs of DNA. Thus the protein coding sequence of the luciferase gene cassette would be expected to contain a large number of covalently modified guanine residues (~12–50 labels). To determine the effect of the covalent attachment of rhodamines on gene expression, luciferase activity of the modified plasmid DNA was compared to the similarly transfected unmodified plasmid DNA. From these experiments we found that covalently modified pCILuc was expressed at levels similar to unmodified pCILuc.

| DNA Transfected | Luciferase Expression in liver (Relative to unmodified pCILuc) |
| --- | --- |
| Naked DNA (pCILuc) | 1.0 |
| pCILuc-Rhodamine (0.2:1 labeling ratio, LabelIT ® rhodamine:pDNA) | 0.47 |
| pCILuc-Rhodamine (0.1:1 labeling ratio, LabelIT ® rhodamine:pDNA) | 0.80 |
| pCILuc-Rhodamine (0.05:1 labeling ratio, LabelIT ® rhodamine:pDNA) | 0.88 |

EXAMPLE 2

DNA chemically modified with DNP using a modifying chemical non-covalent attachment (cis-platinum) is expressed in COS7 cells following transfection as efficiently as unmodified DNA.

Methods.

DNA labeling—dinitophenol (DNP) molecules were attached to plasmid DNA (pCILuc) encoding the reporter gene luciferase through a cis-platinum reaction. The plasmid, pCILuc was mixed with the labeling reagent (Versitag, NEN) at a 0.1:1 ratios (vol:wt) and incubated for 30 minutes at 85° C. DNP-labeled DNA was purified and concentrated by ethanol precipitation.

Luciferase expression—For gene expression studies DNP-labeled DNA was complexed with the transfection reagent TransIT LT-1 (Mirus Corporation) at a 1:3 (wt:vol) ratio and added to COS7 cells according to manufacturer's recommendations. Transfected cells were grown at 37° C. for 48 hours and harvested into luciferase buffer (0.1M KPO4, pH 7.8; 1 mM DTT; 0.1% Triton X-100). Cell lysates were assayed for luciferase activity on a luminometer (Lumat LB 9507, EG&G Berthold).

Results.

Versitag-DNP facilitates the attachment of DNP molecules primarily at guanine nucleotides so labeling occurs throughout the plasmid. To determine the effect of the non-covalent DNP attachment on gene expression, luciferase activity of the modified plasmid DNA was compared to the similarly transfected mock-labeled plasmid DNA. From these experiments we found that DNP modified pCILuc using a modifying chemical non-covalent attachment was expressed at about 50% that of unmodified pCILuc.

| DNA Transfected | Luciferase Expression COS7 cells. (Relative to mock pCILuc) |
| --- | --- |
| Mock labeled DNA (pCILuc) | 1.0 |
| pCILuc-DNP (0.1:1 labeling ratio, Versitag-DNP:pDNA) | 0.49 |

EXAMPLE 3

DNA covalently modified (alkylated) with digoxin is efficiently expressed in mouse liver hepatocytes following in vivo delivery.

Methods:

DNA Labeling—LabelIT®digoxin (Mirus Corporation, Madison Wis.) was used to covalently attach digoxin molecules to a plasmid DNA encoding the reporter gene luciferase (pCILuc). Three different labeling ratios were used to achieve varying amounts of plasmid labeling (0.1:1, 0.05:1, 0.025:1 wt:wt labeling reagent to DNA). The digoxin labeled DNAs was purified and concentrated by ethanol precipitation. Labeling was confirmed by agarose gel electrophoresis in which a mobility shift of all labeled DNA was observed (data not shown).

In vivo gene delivery—Digoxin-labeled and unlabeled pCI-Luc was delivered into mice via tail vein injections (Zhang et al., Human Gene Therapy, Vol. 10 (1999)). Briefly, labeled or unlabeled DNA in a physiologic salt solution was rapidly injected (2.5 ml solution in ~7 seconds) into the tail vein of ~25 g ICR mice (Harlan Sprague Dawley, Indianapolis, Ind.). Animals were sacrificed 1 day after injections and the livers surgically removed. Livers were homogenized in luciferase buffer (0.1M KPO4, pH 7.8; 1 mM DTT; 0.1% Triton X-100) and assayed for luciferase activity on a luminometer (Lumat LB 9507, EG&G Berthold).

Results:

The luciferase encoding plasmid DNA, pCILuc, was covalently labeled with varying amounts of digoxin and compared to unmodified pCILuc in in vivo gene delivery assays. In concordance with the in vitro transfections, covalently modified pCILuc expressed luciferase at least as efficiently as unmodified pCILuc.

| DNA Injected | Luciferase Expression in liver (Relative to unmodified pCILuc) |
| --- | --- |
| Naked DNA (pCILuc) | 1.0 |
| pCILuc-digoxin (0.1:1 labeling ratio, LabelIT ® digoxin:pDNA) | 2.29 |
| pCILuc-digoxin (0.05:1 labeling ratio, LabelIT ® digoxin:pDNA) | 4.67 |
| pCILuc-digoxin (0.025:1 labeling ratio, LabelIT ® digoxin:pDNA) | 1.87 |

EXAMPLE 4

DNA covalently modified (alkylated) with biotin is efficiently expressed in mouse liver hepatocytes following in vivo delivery.

Methods:

DNA Labeling—LabelIT®biotin (Mirus Corporation, Madison Wis.) was used to covalently attach biotin molecules to a plasmid DNA encoding the reporter gene luciferase (pCILuc). Four different labeling ratios were used to achieve varying amounts of plasmid labeling. The biotin labeled DNAs was purified and concentrated by ethanol precipitation. Labeling was confirmed by agarose gel electrophoresis in which a mobility shift of all labeled DNA was observed (data not shown).

In vivo gene delivery—Biotin-labeled and unlabeled pCI-Luc was delivered into mice via tail vein injections (Zhang et al., Human Gene Therapy, Vol. 10 (1999)). Briefly, labeled or unlabeled DNA in a physiologic salt solution was rapidly injected (2.5 ml solution in ~7 seconds) into the tail vein of ~25 g ICR mice (Harlan Sprague Dawley, Indianapolis, Ind.). Animals were sacrificed 1 day after injections and the livers surgically removed. Livers were homogenized in luciferase buffer (0.1M KPO4, pH 7.8; 1 mM DTT; 0.1%

Triton X-100) and assayed for luciferase activity on a luminometer (Lumat LB 9507, EG&G Berthold).

Results:

The luciferase encoding plasmid DNA, pCILuc, was covalently labeled with varying amounts of biotin and compared to unmodified pCILuc in in vivo gene expression assays. Following intravascular delivery (tail vein injection) to liver hepatocytes, biotinylated pCILuc was expressed at least as efficiently as unmodified pCILuc.

| DNA Injected | Luciferase Expression in liver (Relative to unmodified pCILuc) |
|---|---|
| Naked DNA (pCILuc) | 1.0 |
| pCILuc-biotin (0.2:1 labeling ratio, LabelIT ® biotin:pDNA) | 0.87 |
| pCILuc-biotin (0.1:1 labeling ratio, LabelIT ® biotin:pDNA) | 3.25 |
| pCILuc-biotin (0.05:1 labeling ratio, LabelIT ® biotin:pDNA) | 5.39 |
| pCILuc-biotin (0.025:1 labeling ratio, LabelIT ® biotin:pDNA) | 1.41 |

EXAMPLE 5

The covalent attachment of a peptide signal (nuclear localizing signal) to an expressible sequence enhances gene expression in vivo.

Methods:

DNA Labeling.

A Nuclear Localizing Sequence peptide SEQ ID NO: 8 (NLS, CPKKKRKVEDG) derived from the SV40 large T antigen and a control peptide were covalently attached to a DNA reactive compound (LabelIT®-Amine; Mirus Corporation). LabelIT® is a nitrogen mustard derivative that alkylates nucleic acid, thus forming a covalent bond between the reagent and the nucleic acid. After attachment of peptides to LabelIT®, the LabelIT®-NLS and the LabelIT®-control peptide were reacted with plasmid DNA (pCILuc) at the ratios indicated below. The DNA alkylation reaction facilitated by the LabelIT® compounds results in covalent attachment of the peptides directly to the DNA. In this alkylation reaction the peptides are covalently attached to sequences throughout the plasmid both inside the expressible gene sequence and outside.

Intravascular Injections.

Ten micrograms of covalently modified or control DNA was injected into the tail vein of ICR mice (Harlan Sprague Dawley) as previously described (Zhang et al. Human Gene Therapy, 10:1735–1737). Twenty four hours after injection, livers were excised and cell extracts were prepared and assayed for reporter gene activity (luciferase).

Results:

Plasmid DNA encoding the luciferase gene (pCILuc) was covalently modified via the attachment of a peptide signal SEQ ID NO: 8 (nuclear localizing sequence; CPKKKRKVEDG) or a control peptide SEQ ID NO: 9 (Mirus 017; IAEYIPLETDLG) and injected into the tail vein of mice using an in vivo gene delivery method. All covalently modified plasmid constructs were compared to unmodified pCILuc for gene expression capabilities. Reporter gene expression (luciferase) was assayed in the liver after 24 hours. Both sets of animals that received DNA with covalently attached NLS peptides displayed levels of gene expression higher than both naked DNA controls and DNA modified with a control (non-NLS peptide). Two conclusions can be drawn from these results. 1) The covalent attachment of peptides to expressible sequences does not inhibit gene expression as compared to unmodified plasmid DNA; and 2) the attachment of a functionally active peptide (i.e. NLS) augments gene expression.

| DNA Injected | Luciferase Expression in liver (nanograms) |
|---|---|
| Naked DNA (pCILuc) | 2330 |
| pCILuc-NLS (0.2:1 labeling ratio, peptide:pDNA) | 3720 |
| pCILuc-NLS (0.1:1 labeling ratio, peptide:pDNA) | 3510 |
| pCILuc-control peptide (0.2:1 labeling ratio, peptide:pDNA) | 1440 |
| pCILuc-control peptide (0.1:1 labeling ratio, peptide:pDNA) | 1500 |

EXAMPLE 6

In vivo gene delivery of a covalently modified gene sequence results in an enhanced immune response against the plasmid encoded expressible sequence.

Methods:

DNA labeling—Rhodamine molecules were covalently attached to plasmid DNA (pCILuc) encoding the reporter gene luciferase through an alkylation reaction. The plasmid, pCILuc was mixed with LabelIT®Rhodamine (Mirus Corporation, Madison Wis.) at two different ratios (1:0.2; 1:0.1) (wt:wt) and incubated for 30 minutes at 37° C. Rhodamine-labeled DNA was purified and concentrated by ethanol precipitation. Rhodamine-labeling was confirmed by agarose gel electrophoresis in which a mobility shift of all rhodamine-labeled DNA was observed (data not shown). Rhodamine-labeled and unlabeled pCILuc was delivered into mice via tail vein injections (Zhang et al., Human Gene Therapy, Vol. 10 (1999)). Briefly, labeled or unlabeled DNA in a physiologic salt solution was rapidly injected (2.5 ml solution in ~7 seconds) into the tail vein of ~25 g ICR mice (Harlan Sprague Dawley, Indianapolis, Ind.). Three weeks after injection blood was obtained from each of the injected animals and tested for anti-luciferase antibody production on an ELISA assay.

ELISA assay—Plasma samples were obtained through retro-orbital bleeding at several time points following pDNA delivery. The presence of anti-luciferase antibodies was determined by an indirect ELISA. Plates were coated with luciferase protein (Promega, Madison, Wis.). Serial dilutions of mouse serum were assayed and anti-luciferase antibodies were detected by HRP-conjugated anti-mouse IgG (Sigma, St. Louis, Mo.), followed by TMB color development (Sigma, St. Louis, Mo.).

Results:

To determine if covalent attachment of a compound (rhodamine) to an expressible sequence could augment an antibody response against the encoded antigen, plasmid DNA expressing the luciferase gene (pCILuc) was covalently modified with rhodamine at two different levels of modification and injected into the tail vein of a mouse (see Zhang et al., Human Gene Therapy, Vol. 10 (1999)). Genes delivered using this methodology are expressed efficiently in liver hepatocytes and a number of other organs. Blood was collected at 3 weeks post-injection and serum was assayed for anti-luciferase antibodies.

| Injected DNA | ELISA Reading (450 nm) |
|---|---|
| | Serum dilution (1:100) |
| Background Control | 0.0318 |
| Unlabeled DNA | 0.085 (n = 6) |
| Rhodamine-labeled DNA | 0.1565 (n = 4) |
| Conclusion: | |

As expected, injections of plasmid DNA encoding the luciferase gene resulted in antibody production against the luciferase protein by 3 weeks post-injection. However, the covalent attachment of a compound (rhodamine) at positions both within and outside of the expressible sequence facilitated increased antibody production against the "foreign" antigen (i.e. luciferase) as indicated by the increased ELISA values.

EXAMPLE 7

Formation of novel DNA containing particles following the covalent attachment of polycations to polynucleotides under non-condensing conditions.

Methods:

Synthesis: Label IT® Trimer was prepared by adding 4-[(2-chloroethyl)-methylamino]-benzldehyde was added to the α and ε amino groups of the lysine subunit of (4+) Label IT® via reductive amination. The final product was purified by HPLC.

(4+) Label IT® was prepared by reacting the amine terminus of Mirus' commercially available Label IT®- Amine and Nα,Nε-di-t-BOC-L-Lysine N-hydroxysuccinimide ester (Sigma Chemical Co,). The final product is generated by removal of the BOC protecting groups with trifluoroacetic acid. The final product was purified by HPLC.

Rhodamine (4+) Label IT® was prepared by coupling the amine terminus of Mirus' commercially available Label IT®-Amine with FMOC-Lysine (BOC)OH (NovaBiochem) using carbodiimide chemistry. The BOC group was removed from the ε amino group and the resulting amine was reacted with Nα, Nε-di-t-BOC-L-Lysine N-hydroxysuccinimide ester (Sigma Chemical Co.). Following removal of the FMOC group TAMRA-X, SE (Molecular Probes) was added to the α amino group.

The final product was generated by removing the remaining BOC groups with trifluoroacetic acid, followed by HPLC purification.

DNA labeling with (4+) LabelIT®Monomer. 105 micrograms of plasmid DNA (pCILuc) was labeled with 400 micrograms of the (4+) La LabelIT®-monomer for increasing amounts of time (0, 1, 20, 40, 70, 110, 160 and 240 minutes). The labeling reaction was performed in the presence of 0.5 M NaCl which serves to inhibit the condensation of DNA by the unattached 4+ charged cation. Thus only DNA that has been covalently modified with the reactive LabelIT® will demonstrate retardation upon agarose gel electrophoresis. All samples labeled were electrophoresed on a 0.8% agarose gel and visualized by ethidium bromide staining.

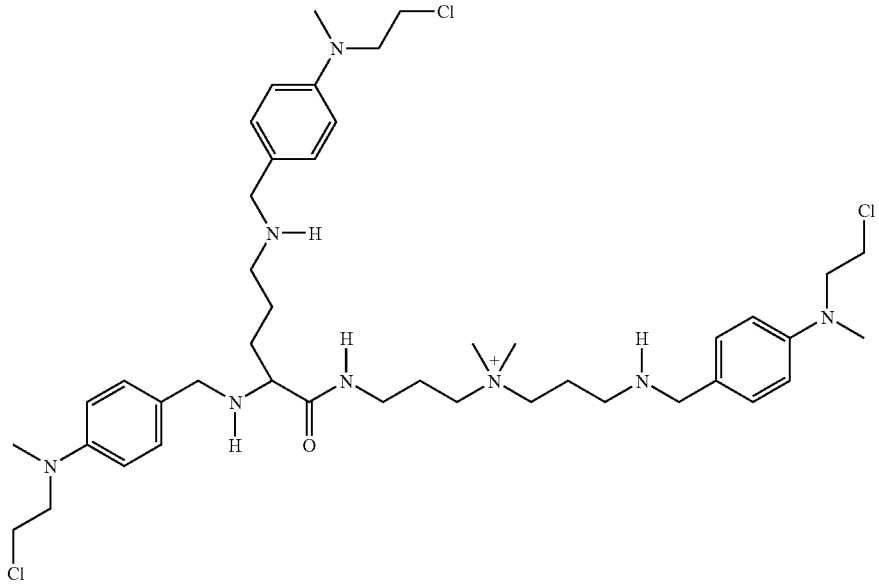

LabelIT® Trimer (4 positive charges)

-continued

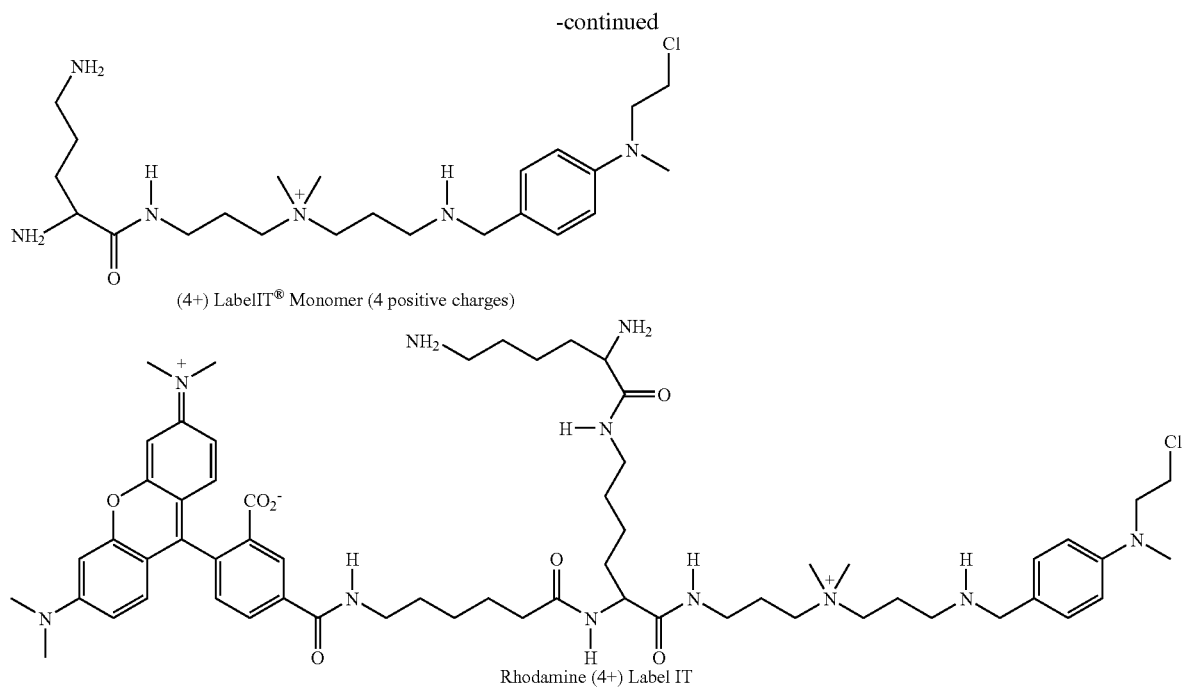

(4+) LabelIT® Monomer (4 positive charges)

Rhodamine (4+) Label IT

Results:

The covalent attachment of cationic compounds containing 4 positive charges results in a DNA conformational change. The level of conformational change increases as a function of time. By 240 minutes all the plasmid DNA has a dramatically altered conformation in which the majority of the DNA is retarded in the gel (see FIG. 1) during electrophoresis. Without the stable attachment of the oligocations to the DNA (in the presence of 0.5 M NaCl), no DNA conformational change is observed.

EXAMPLE 8

DNA particles formed by the covalent attachment of polycations using the LabelIT®Trimer facilitate efficient gene expression in vivo.

Methods:

DNA Labeling—LabelIT®Trimer was used to covalently modify plasmid DNA encoding the reporter gene luciferase (pCILuc). Plasmid DNA was mixed with 3 different concentrations of LabelIT®Trimer (40, 90, and 200 ug) and allowed to incubate for 2 hours at 20° C. and 12 hours at 4° C. Labeling was confirmed by agarose gel electrophoresis in which a mobility shift of all labeled DNA was observed.

Atomic Force Microscopy—Particlesprepared using 175 micrograms of pDNA and 90 micrograms of LabelIT®Trimer were diluted to 1 mg/ml DNA, dried onto grids, and analyzed for size and shape using a Digital Instruments Nanoscope Scanning Prove Microscope.

In vivo gene delivery—Fifty micrograms of trimer-labeled and unlabeled pCILuc was delivered into mice via tail vein injections (Zhang et al., Human Gene Therapy, Vol. 10 (1999)). Briefly, labeled or unlabeled DNA in a physiologic salt solution was rapidly injected (2.5 ml solution in ~7 seconds) into the tail vein of ~25 g ICR mice (Harlan Sprague Dawley, Indianapolis, Ind.). Animals were sacrificed 1 day after injections and the livers surgically removed. Livers were homogenized in luciferase buffer (0.1M KPO4, pH 7.8; 1 mM DTT; 0.1% Triton X-100) and assayed for luciferase activity on a luminometer (Lumat LB 9507, EG&G Berthold).

Results:

Plasmid DNA encoding the luciferase gene (pCILuc) was covalently modified via the attachment of a trifunctional DNA reactive polycation. Attachment of this trimer facilitates a conformational change in the structure of the DNA as observed in agarose gel electrophoresis. To determine the exact conformation the covalently modified DNA was adopting, atomic force microscopy was used to visualize the particles (see AFM below). From this analysis it was found that the covalent attachment of oligocations of 4+ charges resulted in a range of stable spheroid particles of between approximately 20 and 350 nanometers in diameter. To determine if the particles remained functional, all covalently modified plasmid constructs were compared to unmodified pCILuc for gene expression capabilities following in vivo gene delivery into the tail vein of mice. Reporter gene expression (luciferase) was assayed in the various organs after 24 hours.

Figure 2:
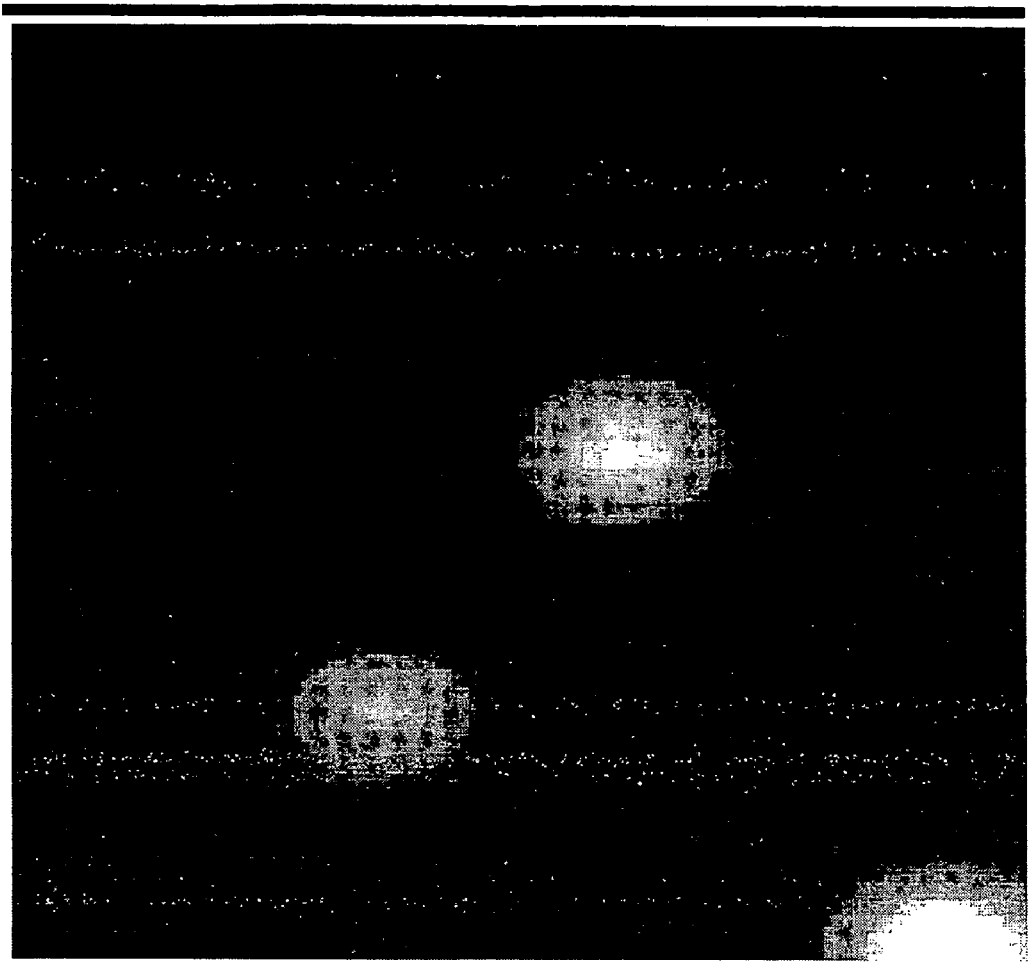
FIG. 2 is a print of Atomic Force Microscopy (AFM) of DNA particles formed by the covalent attachment of LabelIT®—Trimer to plasmid DNA.

See FIG. 2 for Atomic Force Microscopy (AFM) of DNA Particles Formed by the Covalent Attachment of LabelIT®-Trimer to plasmid DNA.

Gene Expression of pDNA Covalently Modified with LabelIT®Trimer

| DNA Injected | Luciferase Expression (Relative to unmodified pCILuc) |
| --- | --- |
| Unmodified DNA (pCILuc) | |
| Liver | 1.0 |
| Spleen | 1.0 |
| Kidney | 1.0 |

-continued

| DNA Injected | Luciferase Expression (Relative to unmodified pCILuc) |
|---|---|
| Heart | 1.0 |
| Lung | 1.0 |
| pCILuc-LabelIT ® Trimer (40 ug Trimer:175 ug pDNA) | |
| Liver | 1.81 |
| Spleen | 2.05 |
| Kidney | 0.72 |
| Heart | 5.30 |
| Lung | 2.79 |

-continued

| DNA Injected | Luciferase Expression (Relative to unmodified pCILuc) |
|---|---|
| pCILuc-LabelIT ® Trimer (90 ug Trimer:175 ug pDNA) | |
| Liver | 0.69 |
| Spleen | 1.83 |
| Kidney | 0.08 |
| Heart | 1.47 |
| Lung | 0.87 |
| pCILuc-LabelIT ® Trimer (200 ug Trimer:175 ug pDNA) | |
| Liver | 0.07 |
| Spleen | 1.14 |
| Kidney | 0.02 |
| Heart | 1.78 |
| Lung | 0.47 |

Conclusions:

In all organs, at the 40 μg level, modified DNA displayed levels of expression comparable to or greater than unmodified DNA. Even at the highest levels of modification, gene expression in the heart and spleen was greater than the unmodified controls. These results indicate that covalent "crosslinking" of a DNA molecule does not inhibit expression and that the change in conformation resulting from this covalent attachment (both within and outside of the expressible sequences) may be beneficial for in vivo gene delivery.

EXAMPLE 9

Compaction of nucleic acids by disulfide exchange of covalently attached sulfhydryl groups.

Methods:

Pyridyldithio-Label IT® was prepared by reacting the amine terminus of Mirus' commercially available Label IT®-Amine with Traut's reagent (Pierce Chemical Co.). The sulfhydryl group that is generated by this reaction was trapped and protected as a pyridyldithio group with Aldrithiol®-2(Aldrich Chemical Co.). The final product was purified via HPLC.

Plasmid DNA (pCI Luc) was modified at a 0.2:1 wt:wt (Label IT®:DNA) ratio using Pyridyldithio-Label IT® (see below). Following labeling the DNA was incubated at 4° C. overnight. The incubation period allows disulfide exchange to take place resulting in cross linked DNA. The modified sample was analyzed by agarose gel electrophoresis.

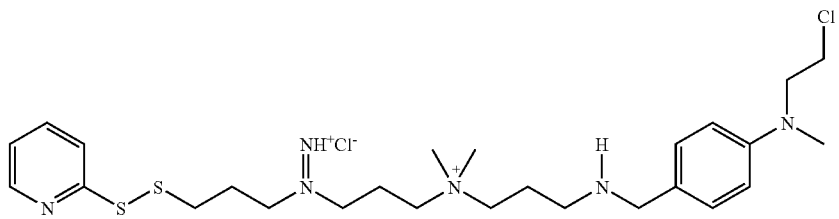

Pyridyldithio-Label IT®

Results:

Following overnight disulfide exchange, the pyridyldithio-Label IT® modified DNA remained in the well while control DNA labeled with bromoacetamide-Label IT® entered the gel in a manner typical of Label IT® modified DNA. (i.e. the modified DNA enters the gel but shows retardation due to charge neutralization caused by the labeling process). This indicates that the pyridyldithio cross-linked DNA formed particles that could not enter the gel (similar to particles formed by crosslinking with the LabelIT® Trimer; see example 7). When DNA was modified with the non-crosslinkable bromoacetamide groups, no particle formation occurs and the DNA migrates into the agarose gel.

EXAMPLE 10

Compaction of nucleic acid by oxidation of covalently attached sulfhydryl groups Plasmid DNA (pCI Luc) was modified at a 0.2:1 wt:wt (Label IT®:DNA) ratio using pyridyldithio-Label IT® (see example 9). The pyridyldithio protecting groups were removed by reduction with TCEP (Pierce Chemical Co.). The nucleic acid was compacted by oxidizing the resulting sulfhydryl groups into disulfide bonds forming intramolecular crosslinks in the plasmid.

Results:

As was observed with disulfide exchange reaction (see example 9), disulfide bond formation facilitated intramolecular crosslinking which resulted in particle formation (complexes did not enter the well during electrophoresis). When the same disulfide crosslinked particles were reduced with DTT, DNA migrated into the gel.

EXAMPLE 11

Covalent attachment of an oligocation (4+ charges) facilitates DNA conformational changes under high salt conditions.

Methods:

Two micrograms of fluorescein labeled DNA (Fl-DNA) was incubated with 20 micrograms of LabelIT®-Trimer (see example 8) in the presence of increasing amounts of unlabeled DNA (5.9, 12.1, 24.4, 49.1, 92.4 micromolar) in 1 ml of buffer consisting of 10 mM HEPES, 500 mM NaCl.

Fluorescence intensity (i.e. fluorescence quenching) of the fluorescein labeled DNA was monitored as a function of time on a Shimadsu fluorescence spectrophotometer (Em 518 nanometers).

Figure 3:
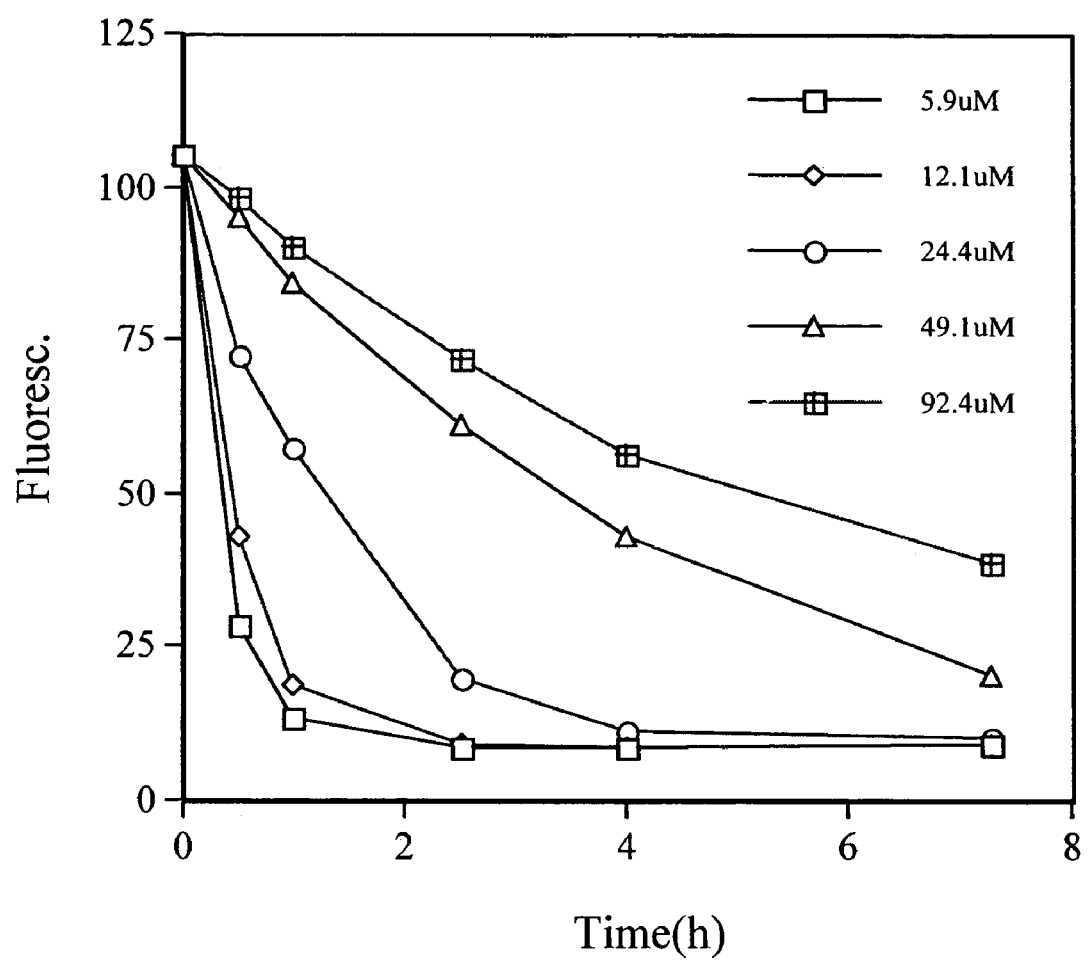
FIG. 3 is a graph illustrating fluorescence vs. time.

Results:

When DNA labeled with fluorescein (or other fluorophores) undergoes conformational change in the form of compaction or condensation, the total emitted fluorescence decreases as a result of fluorescent quenching. This occurs when the fluorophores come in close proximity with each other as happens during DNA collapse. During polycation mediated particle formation, DNA condensation (and hence fluorescent quenching of fluorescein labeled DNA) occurs when the positive to negative charge ratio is >0.9. At ratios of positive to negative charge <0.9, DNA condensation does not occur. To determine if the covalent attachment of oligocations (4+ charge) facilitated fluorescence condensation, fluorescein labeled pDNA was mixed with LabelIT®-Trimer in the presence of increasing amounts of unlabeled pDNA in the presence of 500 mM salt (NaCl). At this concentration of salt, even an excess of the oligocation with 4+ charges will not condense pDNA. However, following the covalent attachment of the LabelIT®-Trimer oligocation to the plasmid DNA, fluorescent quenching of the labeled pDNA (i.e. DNA condensation) occurs at all ratios of positive to negative charges (see FIG. 3).

Conclusions:

Covalent attachment of LabelIT® Trimer (4+ charges) facilitates fluorescent quenching (i.e. DNA compaction) under a wide range of different oligocation to DNA ratios. The fluorescence quenching assay was performed in the presence of 0.5 M NaCl which would prevent non-covalent oligocation mediated DNA condensation at these charge ratios. This indicates that the covalent attachment of the oligocation facilitates the formation of a novel condensed-DNA containing particle and supports the observations of the other examples.

The foregoing is considered as illustrative only of the principles of the invention. Further, since numerous modifications and changes will readily occur to those skilled in the art, it is not desired to limit the invention to the exact construction and operation shown and described. Therefore, all suitable modifications and equivalents fall within the scope of the invention.

We claim:

1. A process for delivery of a modified expressible nucleic acid to a cell, comprising:
   a) preparing a nucleic acid molecule having an expressible sequence;
   b) forming an attachment of a compound, having a molecular weight of 60 kD or less, to the N7 position of a guanine within the expressible sequence of the nucleic acid molecule at a ratio of less than 1 modification per 100 base pairs; and,
   c) delivering the nucleic acid to a cell wherein expression of the expressible sequence is greater than 50% of the level of expression obtained from the expressible sequence not having a modifying chemical attachment.

2. The process of claim 1 wherein the compound comprises a nucleic acid transfer enhancing signal.

3. The process of claim 2 wherein the nucleic acid transfer enhancing signal is selected from the group consisting of a nuclear localizing signal, a ligand that binds a receptor, and a releasing signal.

4. The process of claim 1 wherein the compound is selected from the group consisting of: an enhanced immune response molecule, an antigen, an antibody, a hapten, a membrane active compound, a peptide, a polymer, a polyion, and a fluorescent compound.

5. The process of claim 1 wherein forming an attachment comprises modifying the nucleic acid using an alkylating molecule.

6. The process of claim 5 wherein the alkylating molecule is selected from the group consisting of a mustard and a 3-membered ring system.

7. The process of claim 6 wherein the mustard is selected from the group consisting of a nitrogen mustard and a sulfur mustard.

8. The process of claim 6 wherein the 3-membered ring system is selected from the group consisting of aziridines, oxiranes, cyclopropyls, and episulfides.

9. The process of claim 7 wherein the nitrogen mustard consists of an R-chloride derivative.

10. The process of claim 6 wherein the 3-membered ring system consists of a CPI moiety.

11. The process of claim 1 wherein the nucleic acid consists of double-stranded and single stranded DNA.

12. The process of claim 1 wherein forming an attachment comprises forming a Lewis acid:Lewis base complex between the compound and the nucleic acid, wherein the Lewis acid is not hydrogen.

13. A The process of claim 12 wherein the Lewis acid is a transition metal.

14. A The process of claim 13 wherein the Lewis acid is platinum.

* * * * *